United States Patent [19]

Condon et al.

[11] Patent Number: 5,492,884
[45] Date of Patent: Feb. 20, 1996

[54] 1-[2-(CYCLOPROPYLCARBONYL)-4-FLUOROPHENYL]SULFAMOYL)-3-(4,6-DIMETHOXY-2-PYRIMIDINYL) UREA AND ITS HERBICIDAL METHOD OF USE

[75] Inventors: Michael E. Condon, Lawrenceville; Philip Mark Harrington, Cranbury, both of N.J.

[73] Assignee: American Cyanamid Company, Wayne, N.J.

[21] Appl. No.: 236,718

[22] Filed: Apr. 29, 1994

[51] Int. Cl.$^6$ .................. C07D 239/47; C07D 239/69; A01N 43/54
[52] U.S. Cl. .................. 504/214; 544/321
[58] Field of Search .................. 504/214; 544/321

[56] References Cited

U.S. PATENT DOCUMENTS 4,622,065  11/1986  Van Gemert .................. 544/321
5,009,699  4/1991  Brady et al. .................. 504/212
5,280,007  1/1994  Kawai .................. 544/321

*Primary Examiner*—John M Ford
*Attorney, Agent, or Firm*—Gregory M. Hill

[57] ABSTRACT

The present invention provides 1-{[2-(cyclopropylcarbonyl)-4-fluorophenyl] sulfamoyl}-3-(4,6-dimethoxy-2-pyrimidinyl) urea which has the structural formula I

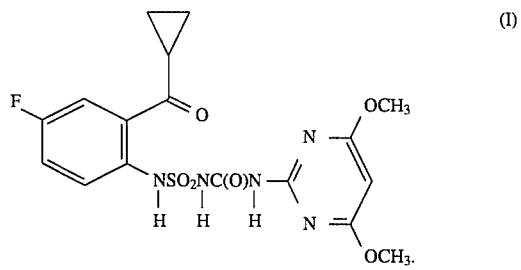

Further provided are compositions and methods comprising that compound for the control of undesirable plant species.

4 Claims, No Drawings

1-[2-(CYCLOPROPYLCARBONYL)-4-FLUOROPHENYL] SULFAMOYL)-3-(4,6-DIMETHOXY-2-PYRIMIDINYL) UREA AND ITS HERBICIDAL METHOD OF USE

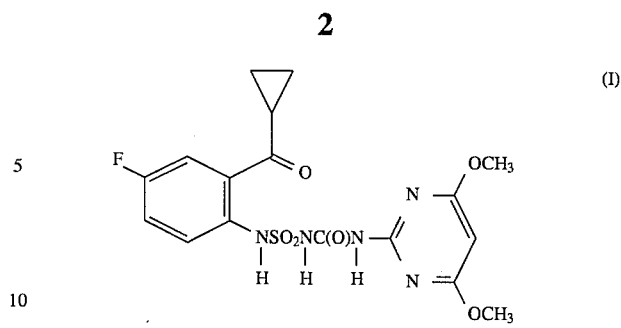

BACKGROUND OF THE INVENTION

Weeds cause tremendous global economic losses by reducing crop yields and lowering crop quality. In the United States alone, agronomic crops must compete with hundreds of weed species. In particular, barnyard-grass, broadleaf weeds and sedges cause extensive economic losses.

U.S. Pat. No. 5,280,007 discloses certain sulfamoyl urea herbicides. However, that patent does not specifically disclose the compound of the present invention.

It is therefore an object of the present invention to provide a compound which is highly effective for controlling undesirable plant species.

It is also an object of the present invention to provide a method for controlling undesirable plant species.

These and other objects of the present invention will become more apparent from the detailed description thereof set forth below.

SUMMARY OF THE INVENTION

The present invention relates to 1-{[2-(cyclopropylcarbonyl)-4-fluorophenyl] sulfamoyl}-3-(4,6-dimethoxy-2-pyrimidinyl)urea.

This invention also relates to a method for using 1-{[2-(cyclopropylcarbonyl)-4-fluorophenyl]sulfamoyl}-3-(4,6-dimethoxy-2-pyrimidinyl)urea to control undesirable plant species.

DETAILED DESCRIPTION OF THE INVENTION

Advantageously, the present invention provides a method for controlling undesirable plant species by applying to the foliage of said plants, or to the soil or water containing seeds or other propagating organs thereof, a herbicidally effective amount of 1-{[2-(cyclopropylcarbonyl)-4-fluorophenyl] sulfamoyl}-3-(4,6-dimethoxy-2-pyrimidinyl)urea.

Surprisingly, it has been found that among the 1-{[2-(cyclopropylcarbonyl) (4-substituted) phenyl]sulfamoyl}-3-(4,6-dimethoxy-2-pyrimidinyl)urea compounds 1-{[2-(cyclopropylcarbonyl)-4-fluorophenyl]sulfamoyl}-3-(4,6-dimethoxy-2-pyrimidinyl)urea provides a higher level of weed control.

The 1-{[2-(cyclopropylcarbonyl)-4-fluorophenyl]sulfamoyl}-3-(4,6-dimethoxy-2-pyrimidinyl)urea compound of the present invention has the following structural formula I:

Advantageously, it has been found that 1-{[2-(cyclopropylcarbonyl)-4-fluorophenyl]sulfamoyl}-3-(4,6-dimethoxy-2-pyrimidinyl)urea is especially useful for the selective control of barnyardgrass, broadleaf weeds and sedges in the presence of cereal crops.

1-{[2-(Cyclopropylcarbonyl)-4-fluorophenyl]sulfamoyl}-3-(4,6-dimethoxy-2-pyrimidinyl)urea may be prepared by reacting 2-amino-4,6-dimethoxypyrimidine with chlorosulfonyl isocyanate in the presence of methylene chloride followed by treatment of the thus prepared reaction mixture with 2-amino-5-fluorophenyl cyclopropyl ketone and triethylamine in the presence of methylene chloride. The reaction scheme is shown in Flow Diagram I.

FLOW DIAGRAM I

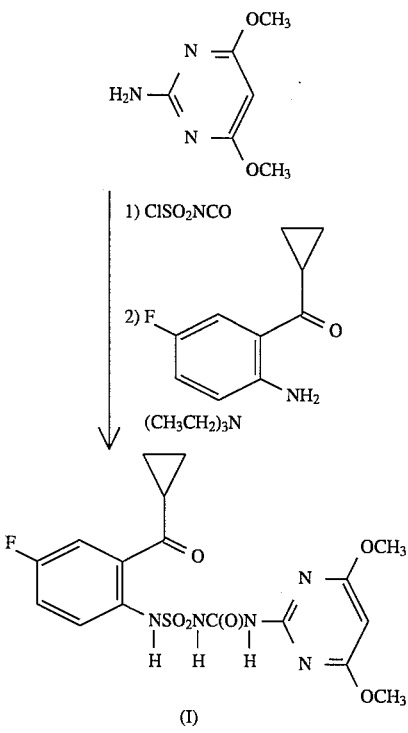

The 1-{[2-(cyclopropylcarbonyl)-4-fluorophenyl]sulfamoyl}-3-(4,6-dimethoxy-2-pyrimidinyl)urea compound of the present invention is an effective herbicidal agent useful for the control of a wide variety of undesirable plant species.. That compound is effective for controlling weeds native to both dry land and wetland areas. That compound is also useful as an aquatic herbicide and is effective in controlling the above-said undesirable plants when applied to the foliage thereof or to the soil or water containing seeds or other propagating organs thereof, such as stolons, tubers or rhizomes, at rates of from about 0.016 to 4.0 kg/ha and preferably from about 0.125 to 1.0 kg/ha. Of course, higher rates may be used to equal effect, but use at such higher rates is deemed to be economically wasteful and environmentally undesirable.

While the compound of the present invention is effective for controlling undesirable plant species when employed alone, it may also be used in combination with other biological chemicals, including other herbicides.

The compound of this invention may be applied in the form of a solid or liquid herbicidal composition, comprising a herbicidally effective amount of the compound dispersed or dissolved in an agronomically acceptable solid or liquid carrier. The formulations may be applied as preemergence or postemergence treatments.

Advantageously, 1-{[2-(cyclopropylcarbonyl)-4-fluorophenyl]sulfamoyl}-3-(4,6-dimethoxy-2-pyrimidinyl)urea may be formulated as an emulsifiable concentrate, a wettable powder, a granular formulation, a flowable concentrate or the like.

In order to facilitate a further understanding of the invention, the following examples are presented primarily for the purpose of illustrating more specific details thereof. The invention should not be deemed limited by the examples as the full scope of the invention is defined in the claims. The term NMR designates nuclear magnetic resonance.

EXAMPLE 1

Preparation of 2-Amino-5-fluorophenyl cyclopropyl ketone

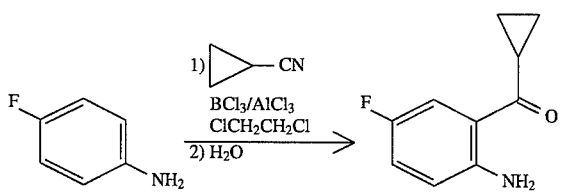

4-Fluoroaniline (5.0 g, 45 mmol), cyclopropyl cyanide (5.0 mL, 68 mmol) and aluminum chloride (6.6 g, 49.5 mmol) are added sequentially to a mixture of boron trichloride (45 mL of a 1.0M solution in methylene chloride) and 1,2-dichloroethane (50 mL) at 0° C. The reaction mixture is warmed to room temperature, distilled until the pot temperature reaches 70° C., refluxed for 18 hours, cooled and diluted with water. The aqueous mixture is extracted with methylene chloride. The organic extracts are combined, dried over anhydrous sodium sulfate and concentrated in vacuo to give the title product as an orange oil (4.1 g, 51%) which is identified by NMR spectral analysis.

Using essentially the same procedure, but employing the appropriately substituted aniline, the following compounds are obtained:

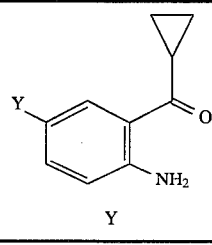

| Y |
|---|
| $CH_3$ |
| $CH_3CH_2$ |
| $Cl$ |

EXAMPLE 2

Preparation of 1-{[2-(Cyclopropylcarbonyl)-4-fluorophenyl]sulfamoyl}-3-(4,6-dimethoxy-2-pyrimidinyl)urea

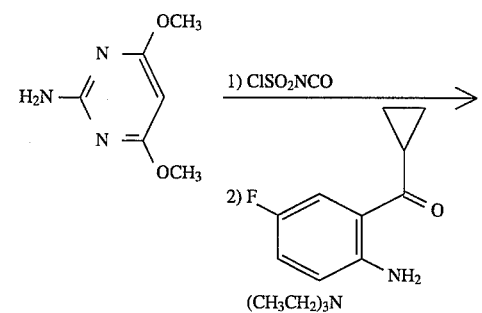

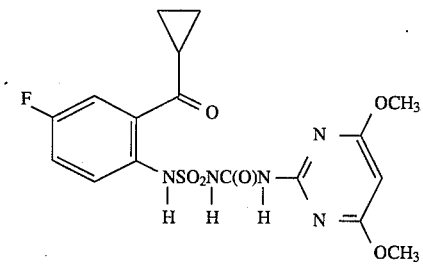

Chlorosulfonyl isocyanate (2.0 mL, 3.25 g, 23.0 mmol) is added to a solution of 2-amino-4,6-dimethoxypyrimidine (4.13 g, 26.6 mmol) in methylene chloride at 0° C. The resulting mixture is stirred for 30 minutes and a solution of 2-amino-5-fluorophenyl cyclopropyl ketone (4.77 g, 26.6 mmol) and triethylamine (6.3 mL, 4.57 g, 45.2 mmol) in methylene chloride is slowly added to the mixture. The resulting solution is stirred at room temperature for 18 hours, concentrated in vacuo and dissolved in methanol. The methanol solution is adjusted to about pH 1 with 10% hydrochloric acid and extracted with methylene chloride. The combined organic extracts are dried over anhydrous sodium sulfate and concentrated in vacuo to obtain a residue. Flash column chromatography of the residue using silica gel and 30% to 50% ethyl acetate in hexanes solutions affords a residue which is crystallized from an ether/petroleum ether solution to give the title product as a pale yellow solid (2.83 g, 24%, mp 76°–78° C.).

Using essentially the same procedure, but employing the appropriately substituted 2-aminophenyl cyclopropyl ketone, the following compounds are obtained:

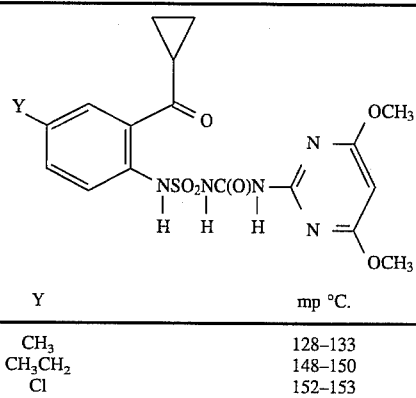

| Y | mp °C. |
|---|---|
| CH$_3$ | 128–133 |
| CH$_3$CH$_2$ | 148–150 |
| Cl | 152–153 |

EXAMPLE 3

Preemergence herbicidal evaluations

The preemergence herbicidal activity of the test compounds is exemplified by the following tests in which the seeds of a variety of monocotyledonous and dicotyledonous plants are separately mixed with potting soil and planted on top of approximately one inch of soil in separate pint containers. After planting, the containers are sprayed with the selected aqueous acetone solutions containing test 3compounds in sufficient quantity to provide the equivalent of about 0.125 to 1.0 kg per hectare of test compound per container. The treated containers are then placed on greenhouse benches, watered and cared for in accordance with conventional greenhouse procedures. From four to five weeks after treatment, the tests are terminated and each container is examined and rated according to the rating system set forth below. The data obtained are reported in Table I.

Test compounds evaluated in this example and in the following example are assigned a compound number. Data in Table I are reported by compound number.

Plant species employed in this preemergence evaluation and in the postemergence evaluation in the following example are reported by header abbreviation, common name and scientific name.

PLANT SPECIES EMPLOYED IN HERBICIDAL EVALUATIONS

| Header Abb. | Common Name | Scientific Name |
|---|---|---|
| ABUTH | Velvetleaf | *ABUTILON THEOPHRASTI*, MEDIC. |
| AMBEL | Ragweed, Common | *AMBROSIA ARTEMISIIFOLIA*, L. |
| CAGSE | Bindweed, Hedge | *CALYSTEGIA SEPIUM* |
| CHEAL | Lambsquarters, Common | *CHENOPODIUM ALBUM*, L. |
| IPOSS | Morningglory, Spp. | *IPOMOEA SPP.* |
| SINAR | Mustard, Wild | *BRASSICA KABER*, (DC) L. C. WHEELR |
| ECHCG | Barnyardgrass | *ECHINOCHLOA CRUS-GALLI*, (L) BEAU |
| CYPRO | Nutsedge, Purple | *CYPERUS ROTUNDUS*, L. |
| SOLNI | Nightshade, Black | *SOLANUM NIGRUM*, L. |

Herbicide Rating Scale

Results of herbicide evaluation are expressed on a rating scale (0–9). The scale is based upon a visual observation of plant stand, vigor, malformation, size, chlorosis and overall plant appearance as compared with an untreated control.

| Rating | Meaning | % Control Compared to Check |
|---|---|---|
| 9 | Complete Kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| — | No Evaluation | |

COMPOUNDS EMPLOYED IN HERBICIDAL EVALUATIONS

| Compound Number | |
|---|---|
| 1 | 1-{[2-(Cyclopropylcarbonyl)-4-fluorophenyl]-sulfamoyl}-3-(4,6-dimethoxy-2-pyrimidinyl)-urea |
| 2 | 1-{[4-Chloro-2-(cyclopropylcarbonyl)phenyl]-sulfamoyl}-3-(4,6-dimethoxy-2-pyrimidinyl)-urea |
| 3 | 1-{[2-(Cyclopropylcarbonyl)-4-methylphenyl]-sulfamoyl}-3-(4,6-dimethoxy-2-pyrimidinyl)-urea |
| 4 | 1-{[2-(Cyclopropylcarbonyl)-4-ethylphenyl]-sulfamoyl}-3-(4,6-dimethoxy-2-pyrimidinyl)-urea |

As can be seen from the data in Table I, the compound of the present invention, 1-{[2-(cyclopropylcarbonyl)-4-fluorophenyl]sulfamoyl}-3-(4,6-dimethoxy-2-pyrimidinyl)urea (compound number 1) is a more effective preemergence herbicidal agent than the comparative compounds (compound numbers 2–4).

TABLE I

Preemergence Herbicidal Evaluation of Test Compounds

| Compound Number | Rate (kg/ha) | ABUTH | AMBEL | CAGSE | CHEAL | IPOSS | SINAR | SOLNI | ECHCG | CYPRO |
|---|---|---|---|---|---|---|---|---|---|---|
| 1 | 1.000 | 9.0 | 9.0 | 9.0 | 9.0 | 9.0 | 8.7 | 9.0 | 7.0 | 9.0 |
|   | 0.500 | 8.0 | 8.0 | 9.0 | 9.0 | 8.7 | 8.7 | 9.0 | 6.5 | 7.5 |
|   | 0.250 | 7.0 | 8.0 | 4.5 | 8.5 | 4.5 | 8.7 | 8.0 | 5.5 | 5.5 |
|   | 0.125 | 4.5 | 7.5 | 4.5 | 7.0 | 3.5 | 8.7 | 6.7 | 3.5 | 3.5 |
| 2 | 0.500 | 2.0 | — | — | 9.0 | 0.0 | 9.0 | 6.0 | 0.0 | 0.0 |
|   | 0.250 | 0.0 | 0.0 | 0.0 | 8.0 | 0.0 | 9.0 | 4.0 | 0.0 | 0.0 |
|   | 0.125 | 0.0 | 0.0 | 0.0 | 7.0 | 0.0 | 9.0 | 0.0 | 0.0 | 0.0 |
| 3 | 0.250 | 3.0 | 2.0 | — | 0.0 | 2.0 | 8.0 | 4.0 | 2.0 | 0.0 |
|   | 0.125 | 0.0 | 0.0 | — | — | 1.0 | 8.0 | 0.0 | 0.0 | 0.0 |
| 4 | 0.250 | 0.0 | 0.0 | — | 0.0 | 0.0 | 0.0 | 0.0 | 0.0 | 0.0 |
|   | 0.125 | 0.0 | 0.0 | — | 0.0 | 0.0 | 0.0 | 0.0 | 0.0 | 0.0 |

EXAMPLE 4

Postemergence herbicidal evaluations

The postemergence herbicidal activity of the test compounds is demonstrated by the following tests, wherein a variety of dicotyledonous and monocotyledonous plants are treated with the test compounds, dispersed in aqueous acetone mixtures. In the tests, seedling plants are grown in jiffy flats for about two weeks. The test compounds are dispersed in 50/50 acetone/water solutions containing 0.5% TWEEN®20, a polyoxyethylene sorbitan monolaurate surfactant of Atlas Chemical Industries, in sufficient quantities to provide the equivalent of about 0.125 to 1.0 kg per hectare of test compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system provided in Example 3.

The data obtained are reported in Table II. Where more than one test is involved for a given compound, the data are averaged. Data in Table II are reported by compound number.

As can be seen from the data in Table II, the compound of the present invention 1-{[2-(cyclopropylcarbonyl)-4-fluorophenyl] sulfamoyl}-3-(4,6-dimethoxy-2-pyrimidinyl)urea (compound number 1) is a more effective postemergence herbicidal agent than the comparative compounds (compound numbers 2–4).

TABLE II

Postemergence Herbicidal Evaluation of Test Compounds

| Compound Number | Rate (kg/ha) | ABUTH | AMBEL | CAGSE | CHEAL | IPOSS | SINAR | ECHCG | CYPRO |
|---|---|---|---|---|---|---|---|---|---|
| 1 | 1.000 | 9.0 | 8.0 | 7.0 | 4.0 | 9.0 | 9.0 | 5.0 | 6.0 |
|   | 0.500 | 9.0 | 8.0 | 7.0 | 2.0 | 9.0 | 9.0 | 4.0 | 5.0 |
|   | 0.250 | 9.0 | 8.0 | — | 2.0 | 9.0 | 9.0 | 4.0 | 4.0 |
|   | 0.125 | 9.0 | 8.0 | — | 2.0 | 9.0 | 9.0 | 3.0 | 4.0 |
| 2 | 0.500 | 8.0 | 7.0 | — | 2.0 | 9.0 | 9.0 | 2.0 | 4.0 |
|   | 0.250 | 7.0 | 6.0 | — | 2.0 | 8.0 | 8.0 | 2.0 | 2.0 |
|   | 0.125 | 5.0 | 5.0 | 7.0 | 1.0 | 7.0 | 8.0 | 2.0 | — |
| 3 | 0.250 | 3.0 | 5.0 | — | 7.0 | 4.0 | 9.0 | 0.0 | 0.0 |
|   | 0.125 | 3.0 | 5.0 | — | 7.0 | 4.0 | 9.0 | 0.0 | 0.0 |
| 4 | 0.250 | 0.0 | 0.0 | — | 0.0 | 0.0 | 0.0 | 0.0 | 0.0 |
|   | 0.125 | 0.0 | 0.0 | — | 0.0 | 0.0 | 0.0 | 0.0 | 0.0 |

What is claimed is:

1. 1-{[2-(Cyclopropylcarbonyl)-4-fluorophenyl]sulfamoyl}-3-(4,6-dimethoxy-2-pyrimidinyl) urea.

2. A method for controlling undesirable plant species which comprises applying to the foliage of said plants or to the soil or water containing seeds or other propagating organs thereof, a herbicidally effective amount of 1-{[2-(cyclopropylcarbonyl)-4-fluorophenyl] sulfamoyl}-3-(4,6-dimethoxy-2-pyrimidinyl)urea.

3. The method according to claim 2 which comprises applying 1-{[2-(cyclopropylcarbonyl)-4-fluorophenyl]sulfamoyl}-3-(4,6-dimethoxy-2-pyrimidinyl)urea to the foliage of said plants or to the soil or water containing seeds or other propagating organs thereof at a rate of about 0.016 kg/ha to 4.0 kg/ha.

4. A herbicidal composition which comprises an agronomically acceptable carrier and a herbicidally effective amount of 1-{[2-(cyclopropylcarbonyl)-4-fluorophenyl]sulfamoyl}-3-(4,6-dimethoxy-2-pyrimidinyl)urea.

* * * * *